(12) United States Patent
Esquivel

(10) Patent No.: US 6,433,867 B1
(45) Date of Patent: Aug. 13, 2002

(54) CONTRAST IMAGING METHOD FOR INSPECTING SPECULAR SURFACE DEVICES

(75) Inventor: Oscar Esquivel, Thousand Oaks, CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 09/481,775

(22) Filed: Jan. 11, 2000

(51) Int. Cl.⁷ .............................................. G01N 21/88
(52) U.S. Cl. .................................................. 356/237.2
(58) Field of Search ................................ 356/600, 446, 356/237.2, 445

(56) References Cited

U.S. PATENT DOCUMENTS

| | | | | |
|---|---|---|---|---|
| 3,396,627 A | * | 8/1968 | Rouy et al. .................. | 356/600 |
| 3,609,044 A | * | 9/1971 | Murphy ....................... | 356/446 |
| 4,299,497 A | * | 11/1981 | Komodromos .............. | 356/448 |
| 4,717,259 A | * | 1/1988 | Suga ........................... | 356/446 |
| 4,846,578 A | * | 7/1989 | Morita et al. ................ | 356/446 |
| 5,334,844 A | * | 8/1994 | Pollard et al. ............... | 250/330 |
| 5,367,174 A | * | 11/1994 | Bazile et al. ................ | 250/572 |
| 5,550,632 A | * | 8/1996 | Harata ......................... | 356/600 |
| 6,111,638 A | * | 8/2000 | Chou et al. ............... | 356/239.2 |
| 6,236,044 B1 | * | 5/2001 | Chou et al. .................. | 250/330 |

* cited by examiner

Primary Examiner—Richard A. Rosenberger
(74) Attorney, Agent, or Firm—Derrick Michael Reid

(57) ABSTRACT

An optical scanning inspection method projects a contrasting patterned image onto a specular mirror-like surface reflecting the contrasting patterned image to a camera that traverses through a range while scanning and recording the reflection that reveals defects and flaws on the specular surface. The defects cause distortion of the reflected pattern to enhance recognition and recording of the defects and flaws. The method is well suited for inspecting large solar cell arrays at a standoff distance.

14 Claims, 2 Drawing Sheets

SEMICONDUCTOR INSPECTION SYSTEM

SEMICONDUCTOR INSPECTION SYSTEM

CONTRASTING PATTERNED IMAGE SCREEN

CONTRASTING ENHANCED FLAWED IMAGE

CONTRAST IMAGING METHOD FOR INSPECTING SPECULAR SURFACE DEVICES

STATEMENT OF GOVERNMENT INTEREST

The invention was made with Government support under contract No. F04701-93-C-0094 by the Department of the Air Force. The Government has certain rights in the invention.

FIELD OF THE INVENTION

The invention relates to the field of semiconductor devices and optical inspection systems. More, particularly, the present invention relates to surface defect detection of semiconductor devices using optical imaging.

BACKGROUND OF THE INVENTION

Solar cell panels have long been used in spacecraft for critical power requirements. The development of a high speed optical method for inspecting solar cells is responsive to a recognized need for a transportable visual inspection method that inspects for solar cell damage in large arrays both at the fabrication facility and after shipment at the launch site. The potential for damage during transport to the launch site and growth of existing cracks beyond acceptable limits remains an important issue, particularly for the more vulnerable, newer generation cells based on thin germanium substrates. Concern over potentially damaged cells has grown with the introduction of the newer thin germanium substrate cells. Typically, individual solar cells are examined during array fabrication using close-up visual techniques that require considerable training and inspection time under dedicated conditions such as close access, appropriate lighting, and optical magnification. Current inspection methods rely on trained inspectors, using aided or unaided visual techniques to examine specimens for cracks, flaws or other irregularities under optimum conditions of lighting, accessibility, and time. An inspector would typically find flaws while searching under low magnification with a mobile light source. Current methods for documenting flaws and cracks generally rely upon hand drawn cell maps or multiple still photographs to document the observed flaw features requiring extensive operator time and training, and is subject to variable human interpretations.

Such inspections insure that critically damaged cells are replaced, and that minor defects are within acceptable parameters prior to launch. Due to constraints of time and access, similar comprehensive inspections of very large arrays after shipment to the launch site are not easily performed. The primary constraints at the launch site are restricted access to the cell surface in that a standoff distance is maintained, and limited time that is available for conventional cell inspection. Hence, there is need for an examination technique that can facilitate the inspection of large arrays at the fabrication site and at the launch site in order to assess possible shipment damage. Currently, there are no automated, image-enhancing, or systematic recording devices to assist and document the solar cell inspection process. Non-standard illumination and detection, such as infrared light and infrared viewing camera has been used to enhance crack detection for high efficiency silicon solar cells that exhibit very low visible light reflectance. This approach alone, however, would not satisfy the concerns for a remote, high rate, inspection process.

U.S. Pat. No. 5,894,345, issued Apr. 13, 1999 to Takamoto entitled "Optical Method of Detecting Defects and Apparatus Used Therein", discloses a linear array line-type source of dotted lines that does not flood a specular surface with a contrasting pattern from a conventional light source. The system detects light emitted from the surface as scattered light as in conventional illumination methods.

U.S. Pat. No. 5,359,416, issued Oct. 25, 1999 to Mueller, entitled "System and Process for Detecting and Monitoring Surface Defects", discloses an inspection system for viewing defects at an angle other than the angle of the expected reflectance, and hence does not take advantage of the reflective specular surface of the device that may contain cracks and flaws.

U.S. Pat. No. 5,091,963, issued Feb. 25, 1992 to Litt, entitled "Method and Apparatus for Inspecting Surfaces for Contrast Variations", discloses the use of contrast variations in reflected light produced by the surface of an article, but does not apply the contrast variations to inspect specular surfaces.

U.S. Pat. No. 5,047,851, issued Sep. 10, 1991 to Sauerrwein, entitled "Process and Device for Detecting and Evaluation Surface Cracks in Workpieces" discloses how conventional inspection images can be digitized and computer processed in a way to distinguish surface cracks, but does not use contrasting illumination patterns to enhance the detectability of small flaws.

U.S. Pat. No. 5,351,078, issued Sep. 27, 1994 to Lemelson, entitled "Apparatus and Method for Automated Observation of Objects" discloses aspects of automating a conventional inspection process where light is focused on the image, but not the reflecting surface.

These cited patents do not address the special difficulty in examining specular surfaces, but are primarily directed to regular, non-mirror-like scattering surfaces that do not take advantage of traversing contrasting reflected patterns that reveal very small and subtle defects and flaws. These and other disadvantages are solved or reduced using the invention.

SUMMARY OF THE INVENTION

An object of the invention is to provide a method for inspecting specular surfaces for flaws and cracks using a contrast illumination pattern.

Another object of the invention is to provide a method for inspecting specular surfaces using a contrast pattern and viewing video camera that concurrently traverse the specular surface for detecting differences in the reflection for locating defects on the specular surfaces.

The present invention relates to the visual inspection of smooth, specular surfaces, that is, mirror-like surfaces having high reflectivity. The inspection method is based on the design and application of contrasting patterned images to enhance the detection of cracks or other physical disruptions such as pits, dents, bumps, particulate contamination, among others, on the surface of specular materials, or specular surfaces that are covered by a transparent material, such as solar cells under coverslips.

The inspection method uses the specular mirror-like surface to image a contrast pattern or lighting mask. The human eye, or the video camera, views the contrasting patterned image reflected by the mirror-like surface focused on the plane of the specular surface. Small cracks or flaws are enhanced because the slight change in the tilt of the surface around the flaw causes the out-of-focus image of the contrast pattern to appear distorted. In order to inspect a specular surface area, the image of the contrast pattern scans or translates across the inspection surface. The flaws are revealed over time as the contrast pattern traverses across the specular surface. Hence, the reflected image usually does not contain a complete flaw or crack in any one instant of time. Contrast variations on a mirror-like inspected specular surface are illuminated by a pattern or mask having a contrast pattern. The contrasting pattern floods the inspection specular surface with conventional illumination for illuminating and viewing the mirror-like specular surface to detect small flaws.

Thus, the camera or human eye and the contrasting pattern light source move relative to the inspection surface, while maintaining a fixed angle of incidence. The inspection method enhances the viewing of defects by gathering reflected light, preferably with a video camera, at an angle that is at an angle of expected reflectance. The camera mechanically traverses an inspection range to maintain the reflection of the pattern in view while scanning. The inspection system detects optically nonhomogeneous portions of the specular surface of the device under test for flaws or cracks by the absence of light reflected at the expected angle of reflectance The inspection method allows a video camera to capture detailed surface imagery of individual devices, such as cells in a large array, employing an illumination contrast pattern during the scan that enhances the image of the non-planar surface around a crack or flaw. With an arrangement of a camera, an illuminator, and a contrasting pattern, the scanning method offers a reproducible, systematic examination process that is independent of the inspection operator or local ambient conditions. A videotaped inspection provides a real image record of flawed conditions. The method offers assured compatibility with launch site environments and helps to facilitate eventual comparison of pre-shipment and post-shipment array conditions to determine whether pre-existing cracks grow beyond acceptable limits, and to assess the extent of new crack formation.

The visible inspection system acquires and stores detailed imagery of the cell and coverslip condition with sufficient spatial resolution and image quality to verify whether small pre-existing cracks have grown beyond acceptable limits, and to determine the extent of new crack formations. The system is amenable to launch site constraints by providing remote or standoff inspection capability, with an image collection time fast enough to make data acquisition at the launch site for subsequent detailed evaluation practical for very large arrays. That is, the system provides a real time continuous video record of the inspection process. The system provides the means to perform the inspection task in a practical time period, to rapidly obtain inspection data even when close access is prohibited and when imaging of flaws is necessary. These and other advantages will become more apparent from the following detailed description of the preferred embodiment.

DETAILED DESCRIPTION OF THE PREFERRED EMBODIMENT

Figure 1:
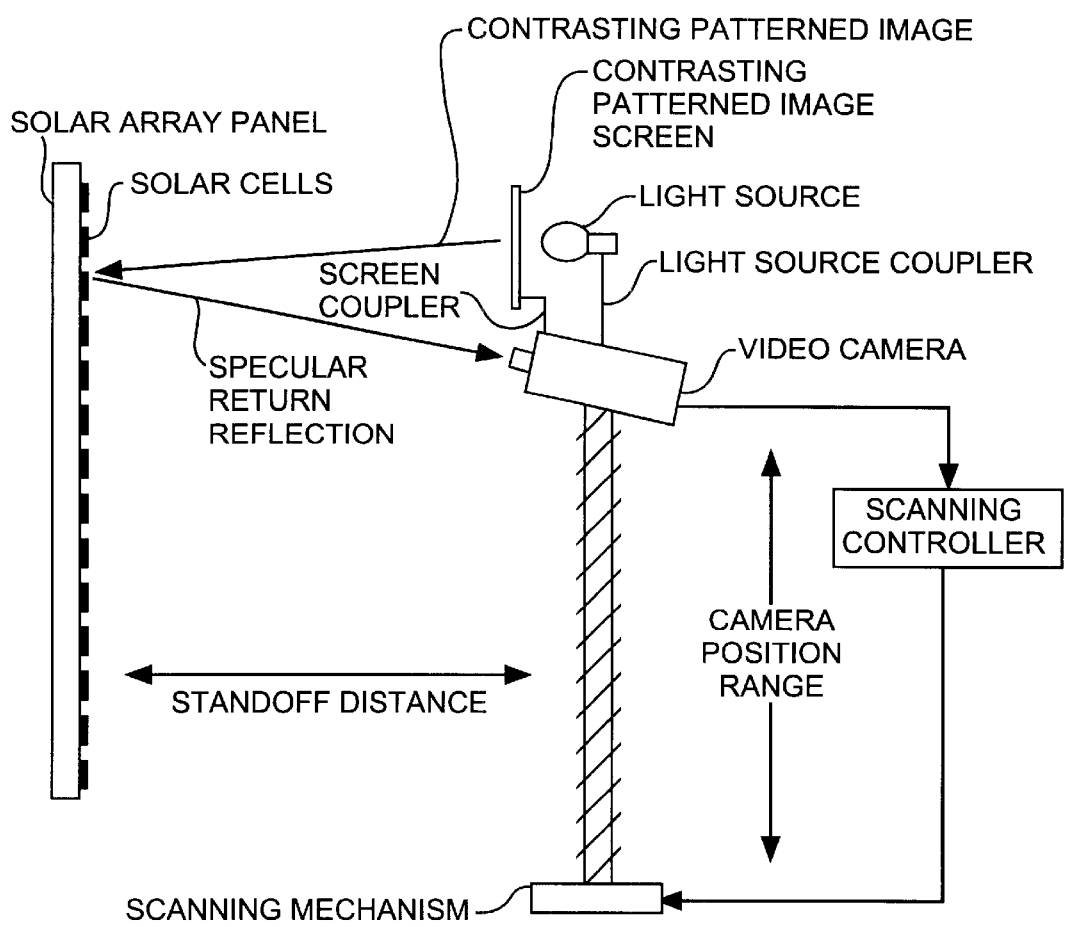
FIG. 1 is a diagram of elements for remote inspection of large solar arrays using contrast imaging.

An embodiment of the invention is described with reference to the figures using reference designations as shown in the figures. Referring to FIG. 1, a semiconductor inspection system is used to optically inspect devices, such as solar cells in a solar array panel. The system includes a light source, a contrasting patterned image screen, and a video camera coupled rigidly together using a screen coupler and a light source coupler. The screen, source, and camera are affixed to a scanning mechanism that places the screen, source, and camera at a standoff distance from the solar cells and function to traverse the screen, source, and camera through a camera position range during scanning of the solar cells. The light source illuminates the contrasting patterned image screen that then projects an illuminating contrasting patterned image onto the solar cells. The device under inspection, such as the solar cells, has a reflective specular surface that reflects the contrasting pattern image as a specular return reflection that is viewed and recorded by the camera. With the surfaces of the cells aligned in parallel, the angle defined by the contrasting image pattern and the specular return reflection is maintained as the source, screen, and camera traverse the camera position range during scanning. A scanning controller is used to control the scan rate and to record optical images of the flawed specular surface for subsequent or real time evaluations. The camera can be a video recorder that can download the reflected contrasting patterned images to the scanning controller.

Figure 2:
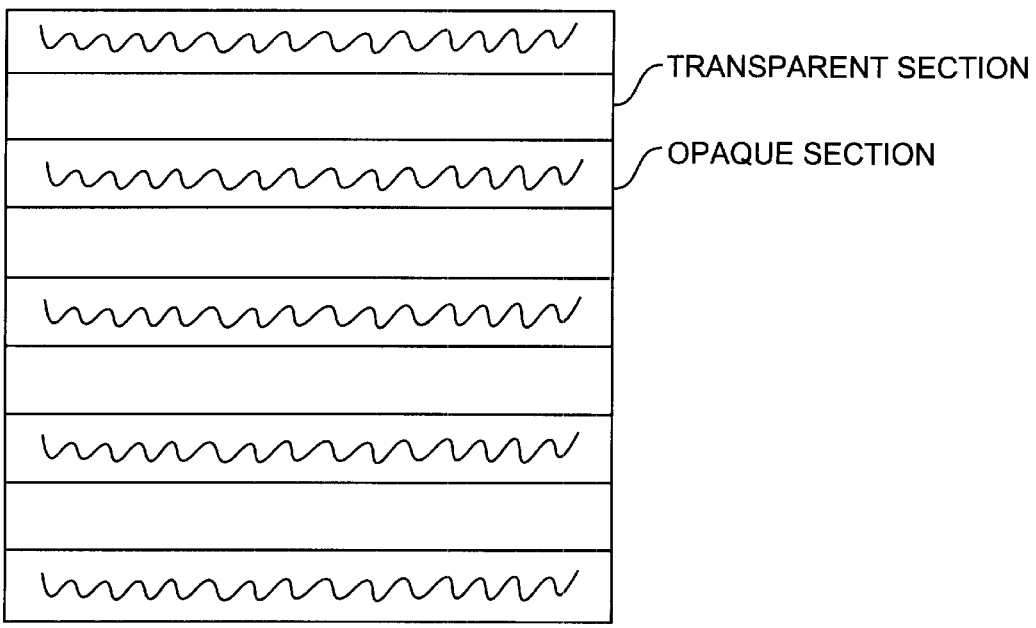
FIG. 2 is a diagram of a contrasting pattern for illuminating specular surfaces under inspection.
Figure 3:
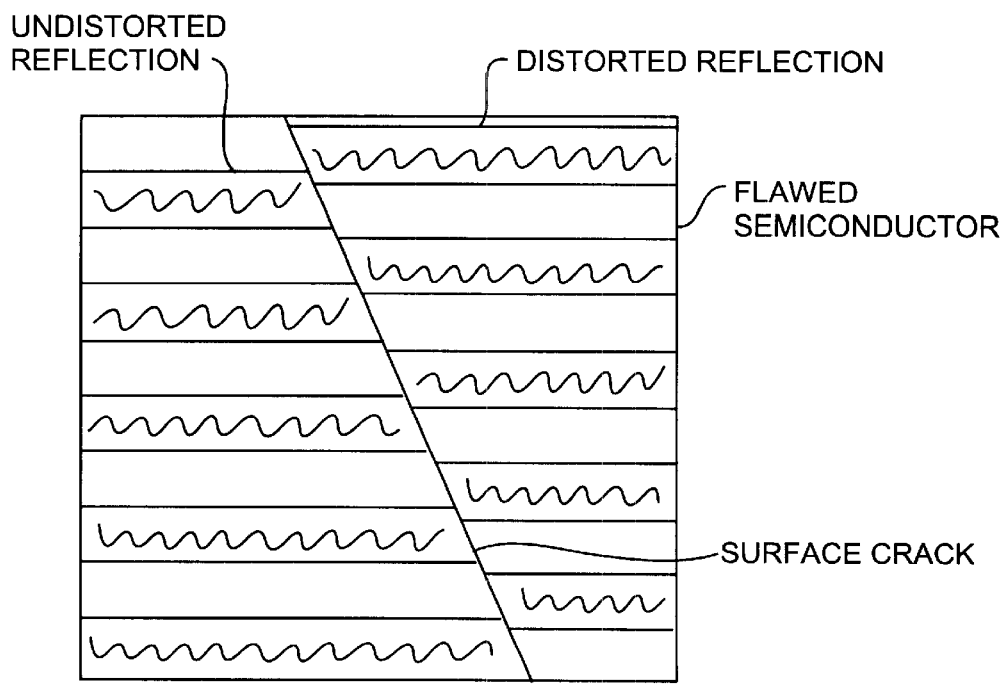
FIG. 3 is a diagram of a reflected contrast image of a flawed semiconductor device revealing a surface crack.

Referring to all of the figures, and particularly to FIGS. 2 and 3, the contrasting patterned image, with an illumination light source behind it, provides an array of light and dark features that are viewed as a reflected image from the specular surface of the device or specimen, such as the solar cells. An exemplar contrasting pattern of horizontal light and dark bars is created by illuminating corresponding transparent and opaque sections of the contrasting patterned screen. The contrasting patterned image is reflected by the specular mirror-like surface of the devices. Where there is a surface defect, such as a surface crack, the reflected image will include both an undistorted reflection and a distorted reflection from the flawed semiconductor. As the light and dark pattern is made to translate across the specimen surface, the non-planar surface around a flaw, bump or pit disrupts the image pattern. The slight tilt in the surface near a crack causes the scanning illuminating contrasting patterned image to scatter differently when compared to the non-cracked surface. The greater the non-planar condition of the surface, the more enhanced the flaw feature becomes. With the appropriate selection of contrasting patterns, such as horizontal stripes, vertical stripes, checkerboard patterns, among many others, the video recording of the moving reflected contrasting patterned image is made from the standoff distance to provide a record of the type of small flaws on the surface. The camera is preferably focused on the specular surface. The sizes of the flaws that can be distinguished by the inspection system are small in scale to the contrasting patterned image, and with a suitably focused and zoomed camera, very small flaws can be imaged.

This inspection system and method uses contrasting patterns to enhance the image of cell cracks for fast, video taped inspection of the device, such as solar cells. In an alternative method, the patterned screen, video camera and light source remain fixed while the specimen under inspection is translated across the field of view, which is equivalent to having the specimen remain fixed, as in the case of a large array, while the patterned screen, video camera, and light source are traversed across the cell field of view through the camera position range. In the preferred form, the illuminating contrasting patterned image and the camera concurrently respectively illuminate and scan the cell at a predetermined cell scan rate. As the camera traverses at the camera position rate, the dark and light patterns move across the cells at the predetermined cell scan rate. Alternatively, to this linear traversing of the cells by the illuminating contrasting patterned image and viewing camera, the illuminating contrasting patterned image can be made to translate at a much higher rate than the cell scan rate characterized by a flicker rate of a rotating patterned screen. In the place of the fixed contrasting patterned screen, a rotating optical chopper wheel may be used to provide high-speed translating light and dark contrast patterns across the specular reflecting surface for enhancing crack imaging.

The inspection method provides an inspection technique for specular surfaces. The system uses contrast image patterns to enhance the detection of small cracks, pits, bumps, and other physical flaws or particulate contamination on the specular surface. The video camera, with optical zoom magnification capability, can inspect the specular surface at a standoff distance. The camera can be coupled with computer processing equipment, such as the scanning controller, for high data rate collection of inspection image data for subsequent detailed evaluation.

The inspection method can be used by commercial contractors involved with the inspection or documentation of the integrity of fragile specular surfaces. The use of this inspection scanning approach reduces the time required for examination, and reduces the personnel training required to detect fine flaws by enhancing their visibility through contrast imaging. In the aerospace industry, solar cells are well suited for such rapid scan inspection at a stand off distance. The method can also be applied for enhancing the image of fingerprints as a flaw on a specular surface. Any surface contamination that results in a change in the angle of reflection by a change in the optical index, is enhanced. Those skilled in the art can make enhancements, improvements, and modifications to the invention, and these enhancements, improvements, and modifications may nonetheless fall within the spirit and scope of the following claims.

What is claimed is:

1. A method for inspecting a cellular specular surface of a solar cell having a covering layer of transparent material having a covering specular surface for cracks in the cellular specular surface and the covering specular surface, the method comprising the steps of, generating an illuminating contrasting patterned image,
   illuminating the cellular specular surface of the solar cell through the covering specular surface by the illuminating contrasting patterned image at a contrasting patterned image angle, the cellular specular surface and the covering specular surface serving to reflect the contrasting patterned image as a reflected contrasting patterned image,
   receiving the reflected contrasting patterned image at a specular return reflection angle, and
   scanning the cellular and covering specular surfaces by illuminating the cellular specular surface and the covering specular surface at the respective contrasting image pattern angle and concurrently receiving the reflected contrasting patterned image at the specular return reflection angle at a plurality of positions through a predetermined position range for generating a respective plurality of the reflected contrasting patterned images, the cracks serving to distort the plurality of reflected contrasting patterned images during scanning.

2. The method of claim 1 wherein the receiving step, the reflected contrasting patterned image is received at a predetermined stand off distance from the cellular specular surface.

3. The method of claim 1 wherein the plurality of reflected contrasting patterned images serve to enhance optical recognition of the cracks from one of the plurality of reflected contrasting patterned images to another one of the plurality of reflected contrasting patterned images.

4. The method of claim 1 wherein the covering layer is a coverslip of the solar cell.

5. The method of claim 1 wherein the covering layer is a coverslip of the solar cell and the cracks are irregularities in the solar cell and in the coverslip.

6. The method of claim 1 wherein the scanning step comprises the step of moving the cellular specular surface relative to the illuminating contrasting patterned image during scanning.

7. The method of claim 1 further comprising the step of recording the plurality of reflected contrasting patterned images during scanning.

8. The method of claim 1 wherein the illuminating contrasting patterned images illuminates during scanning at a predetermined scan rate across the cellular specular surface, the method further comprising the step of, rotating the illuminating contrasting patterned image for increasing the scan rate across the cellular specular surface.

9. A method for inspecting for cracks of a cellular specular surface of a solar cell having a covering layer of transparent material having a covering specular surface, the method comprising the steps of, generating an illuminating contrasting patterned image,
   illuminating the cellular specular surface of the solar cell through the covering specular surface of the covering layer by the illuminating contrasting patterned image at a contrasting patterned image angle, the cellular and covering specular surfaces serving to reflect the contrasting patterned image as a reflected contrasting patterned image,
   receiving the reflected contrasting patterned image at a specular return reflection angle, the reflected contrasting patterned image is received at a predetermined stand off distance from the cellular and covering specular surfaces,
   scanning the surface by concurrent illuminating the specular surface at the respective contrasting patterned image angle and receiving the reflected contrasting patterned image at the specular return reflection angle at a plurality of positions through a predetermined position range for generating a respective plurality of the reflected contrasting patterned images, the cracks serving to distort the plurality reflected contrasting patterned images during scanning, the scanning serving to move the cellular and covering specular surfaces relative to the illuminating contrasting patterned images during scanning, and
   recording the plurality of the reflected contrasting patterned images during scanning, the recorded plurality of reflected contrasting patterned images serve to enhance optical recognition of the cracks from one of the plurality of reflected contrasting patterned images to another one of the plurality of reflected contrasting patterned images.

10. The method of claim 9 wherein the covering layer is a coverslip of the solar cell.

11. The method of claim 9 wherein the covering layer is a coverslip of the solar cell and the cracks are irregularities in the coverslip and in the solar cell.

12. The method of claim 9 wherein the receiving step further comprises the steps of, recording the plurality of reflected contrasting patterned images during the receiving step, and storing the recorded images.

13. The method of claim 9 wherein the recording step a video camera receives and records the plurality of reflected contrasting patterned images.

14. The method of claim 9 wherein the receiving step receives the reflected contrasting patterned images focused upon the cellular specular surface.

* * * * *